United States Patent [19]

Hoffmann et al.

[11] 4,031,141

[45] June 21, 1977

[54] 12-ALKOXY-3,7,11-TRIMETHYL-DODECATETRAENES

[75] Inventors: Werner Hoffmann, Neuhofen; Manfred Baumann, Mannheim, both of Germany

[73] Assignee: BASF Aktiengesellschaft, Ludwigshafen (Rhine), Germany

[22] Filed: July 9, 1976

[21] Appl. No.: 703,956

[30] Foreign Application Priority Data

July 23, 1975 Germany .......................... 2532851

[52] U.S. Cl. ............................ 260/614 R; 252/522; 260/594; 260/615 R; 260/483; 260/484 A
[51] Int. Cl.$^2$ .................. C07C 43/00; C07C 43/14
[58] Field of Search ........................ 260/614 R, 522

[56] References Cited

UNITED STATES PATENTS

| | | | |
|---|---|---|---|
| 3,429,970 | 2/1968 | Ruegg et al. | 260/614 X |
| 3,665,040 | 5/1972 | Ruegg et al. | 260/614 R |
| 3,801,652 | 11/1974 | Ruegg et al. | 260/614 R |
| 3,943,177 | 3/1976 | Helmlinger et al. | 260/614 L |

*Primary Examiner*—Howard T. Mars
*Attorney, Agent, or Firm*—Keil, Thompson & Shurtleff

[57] ABSTRACT

New 12-alkoxy-3,7,11-trimethyl-dodecatetraenes are of interest as perfume and flavor materials having a mandarin and orange effect.

The new compounds can be manufactured relatively simply, e.g. by vinylating or ethynylating the corresponding new, but easily accessible, 7-alkoxy-6-methyl-hept-5-en-2-ones and subsequently partially hydrogenating the products, reacting the resulting allyl alcohols with acetoacetic acid esters or diketenes at an elevated temperature, again vinylating or ethynylating the alkoxyketones obtained, then partially hydrogenating the products, and eliminating water from the 12-alkoxy-3,7,11-trimethyl-3-hydroxy-dodecatrienes thus obtained.

2 Claims, No Drawings

12-ALKOXY-3,7,11-TRIMETHYL-DODECATETRAENES

The present invention relates to new 12-alkoxy-3,7,11-trimethyldodecatetraenes, which are of interest as perfume and flavor materials having a mandarin and orange effect, and to simple processes for the manufacture of the new compounds.

Specifically, the invention relates to compounds of the general formula I

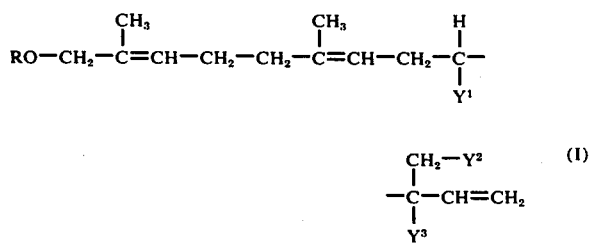

where R is $CH_3$, $C_2H_5$, n-$C_3H_7$ or iso-$C_3H_7$, preferably $CH_3$ or $C_2H_5$, and $Y^1$ and $Y^2$ are different and each is hydrogen or, together with $Y^3$, is an additional bond between the carbon atoms carrying $Y^1$ and $Y^3$, or $Y^2$ and $Y^3$, respectively, and especially to a mixture of the isomeric compounds of the general formulae Ia and Ib

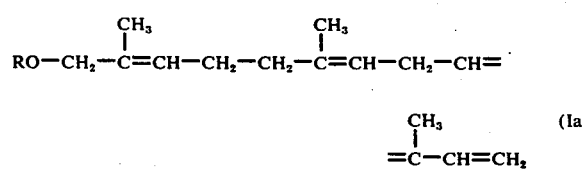

and

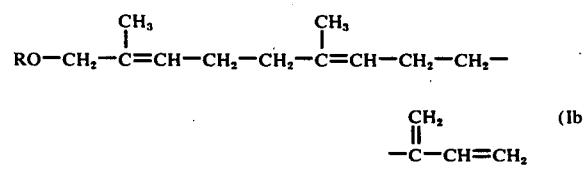

where R is $CH_3$, $C_2H_5$, n-$C_3H_7$ or iso-$C_3H_7$, preferably $CH_3$ or $C_2H_5$.

The new compounds are of interest because of their properties as perfume and flavor chemicals having a mandarin and orange effect. They are of potential importance since they are substantially more easily obtainable than the natural perfume and flavor materials of mandarins and oranges, namely the sinensals. The new compounds differ from the sinensals in having an additional interesting green coniferous note. Furthermore they are substantially less sensitive to oxidation than are the sinensals.

The corresponding new 7-alkoxy-6-methyl-hept-5-en-2-ones are particularly suitable starting compounds for the manufacture of the new compounds. The new 7-alkoxy-6-methyl-hept-5-en-2-ones can be manufactured, for example, by vinylating the corresponding alkoxyacetones in a Grignard reaction and reacting the resulting 1-alkoxy-2-hydroxy-2-methyl-but-3-enes with acetoacetic acid esters at from 150° to 300° C.

The manufacture of the new 12-alkoxy-3,7,11-trimethyl-dodecatetraenes of the formula I from the 7-alkoxy-6-methyl-hept-5-en-2-ones may be carried out in accordance with various simple processes.

For example, they may be manufactured by

A. vinylating or ethynylating, by conventional methods, the 7-alkoxy-6-methyl-hept-5-en-2-ones of the general formula II

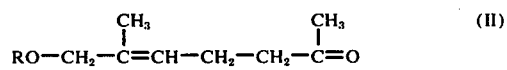

where R has the above meaning, and subsequently partially hydrogenating the products, B. converting the resulting allyl alcohols of the formula III

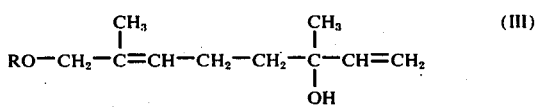

where R has the above meaning, by conventional methods to the corresponding alkoxyketones of the formula IV

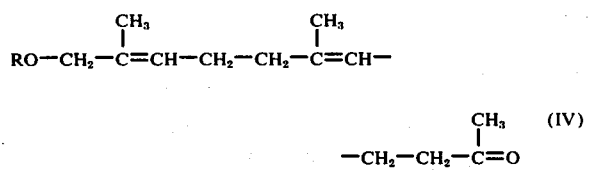

C. again vinylating or ethynylating these by conventional methods and subsequently partially hydrogenating the products and D. eliminating water, by conventional methods, from the resulting allyl alcohols of the formula V

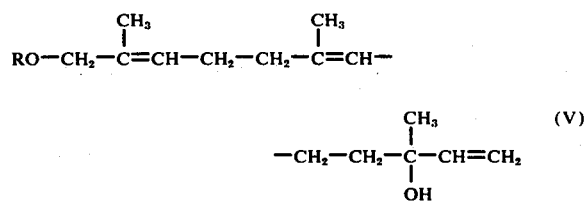

The individual reaction steps will be explained in more detail below.

Aa. Reaction of 7-alkoxy-6-methyl-hept-5-en-2-ones of the formula II with a solution of a vinyl-magnesium halide and hydrolysis of the resulting alcoholate.

Suitable vinyl-magnesium halides are vinyl-magnesium chloride, bromide and iodide, but particularly the first-mentioned. The vinyl-magnesium halide solutions may be manufactured in the conventional manner by reacting vinyl chloride, vinyl bromide or vinyl iodide with magnesium in ether solvents, e.g. diethyl ether, tetrahydrofuran or diethylene glycol dimethyl ether. From 0.5 to 5, preferably from 1 to 2, molar solutions are used. The reaction temperature is from about −20° to +60° C, preferably from 0° to 30° C. In order to achieve as nearly complete conversion of the ketone as possible, it is advisable to use about 10 percent excess of Grignard solution. The alcoholates are hydrolyzed by adding the amount of water required to form the salt. The reaction products may be isolated by filtering or centrifuging and fractionally distilling the organic phase.

Ab. Ethynylation of the 7-alkoxy-6-methyl-hept-5-en-2-ones of the formula II and subsequent partial hydrogenation of the resulting propargyl alcohols.

The ethynylation may be carried out either by reacting the alkoxyketones II with a solution of ethynyl-magnesium halides under the conditions described for the reaction with vinyl-magnesium halides, or by reacting the ketones II with acetylene in inert organic solvents in the presence of heavy metal acetylides such as copper acetylide and silver acetylide, or in the presence of catalysts having a basic reaction, such as sodium acetylide or potassium acetylide, or the oxides, hydroxides, alcoholates, hydrides or amides of the alkali metals or alkaline earth metals, or in the presence of anion exchangers containing quaternary ammonium groups (see, for example, Belgian Pat. No. 725,275). It is particularly advantageous to carry out the reaction with acetylene in the presence of acetylides of sodium, potassium, lithium or magnesium or of compounds which can form these acetylides under the reaction conditions, such as oxides or hydroxides, alcoholates, hydrides or amines of these metals, and in solvents such as diethyl ether, tetrahydrofuran, N-methylpyrrolidone or dimethylformamide.

The ethynylation is carried out at from −20° to +50° C, preferably from 0° to +30° C, and under pressures from normal pressure to about 30 atmospheres. The mixture is worked up, and the reaction products are isolated, by hydrolysis followed by fractional distillation of the organic phase.

The partial hydrogenation of the propargyl alcohols obtained may be carried out in solvents or without solvents.

It is particularly advantageous to carry out the reaction in the presence of alcohols such as methanol or ethanol, ethers such as diethyl ether, tetrahydrofuran or dioxane, and esters such as esters of acetic acid, or methyl propionate.

Particularly suitable catalyst are supported palladium catalysts which contain from 0.01 to 5 percent by weight of palladium.

Carriers which may be mentioned particularly are calcium carbonate, aluminum oxide and silicon dioxide. To increase the selectivity it is advantageous to deactivate the said catalysts, e.g. in accordance with German Pat. No. 1,115,238 by treatment with zinc ions or lead ions.

The hydrogenation is in general carried out under atmospheric pressure or under an excess hydrogen pressure of from 0.1 to 1 atmosphere, and at from about 0° to 80° C, preferably from 15 to 35° C. The products III are isolated by filtration and distillation. B. The conversion of the allyl alcohols of the formula III to the corresponding alkoxyketones of the formula IV can be carried out in accordance with 4 different conventional processes.

1. Reaction of the allyl alcohols of the formula III with acetoacetic acid esters at from 150° to 300° C (cf. J. Chem. Soc. 1940, 704)

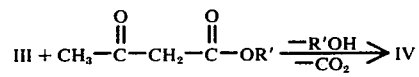

Advantageously, acetoacetic acid esters of alcohols of 1 to 4 carbon atoms are employed in amounts of from 1 to 10 moles, preferably from 1 to 3 moles, per mole of allyl alcohol. The reaction can be carried out without solvents, or in an inert solvent which boils at from 150° to 300° C. Suitable solvents are ethers, e.g. diethylene glycol dimethyl ether, and amines, such as N-methylpyrrolidone and dimethylformamide. The mixtures or solutions of allyl alcohol III and acetoacetic acid esters are heated at from 150° to 300° C, and the alcohol produced during the reaction is continuously distilled off through a column. The course of the reaction can be followed by measuring the carbon dioxide liberated. The products are purified by fractional distillation.

2. Reaction with diketene and pyrolysis of the resulting acetoacetates

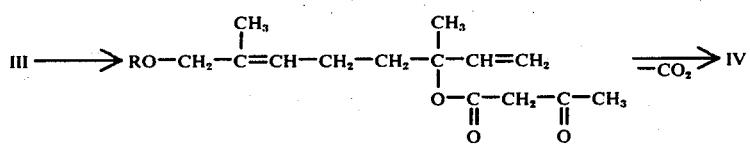

The allyl alcohols III are first mixed with a basic catalyst and then, at from 20° to 100° C, preferably from 30° to 70° C, with diketene, advantageously used in about an equimolar amount. Suitable basic catalysts are strong bases, e.g. hydroxides and alcoholates of the alkali metals, as well as ammonia and its substitution products, e.g. primary, secondary and tertiary amines and pyridine.

The amounts of basic catalysts used are from 0.1 to 5, preferably from 0.5 to 1.5, percent by weight, based on allyl alcohol employed.

The pyrolysis of the acetoacetates formed is carried out at from 150° C to 300° C, preferably from 180° C to 200° C. The products are isolated by fractional distillation.

3. Reaction of the allyl alcohols of the formula III with isopropenyl ethers (cf. G. Saucy and R. Marbet, Helv. Chim. Acta 50 (1967) 2091).

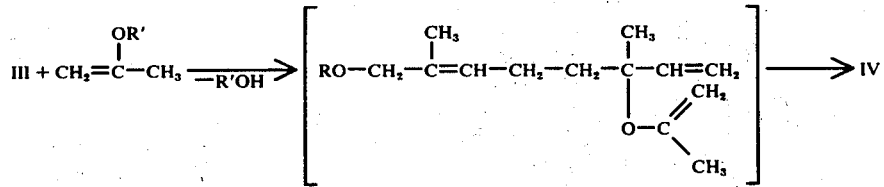

A mixture of the allyl alcohol III with an isopropenyl ether is heated, in the presence of catalytic amounts of an acid, at from 70° C to 250° C, preferably from 120° C to 200° C.

The reaction may be carried out with or without solvents. Suitable solvents are heptane, gasoline, toluene and the like. The reaction time is from 12 to 30 hours. Examples of suitable acids are phosphoric acid, sulfuric acid, p-toluene-sulfonic acid or Lewis acids such as mercury salts. A variant of this reaction is to employ acetone-ketals in place of isopropenyl ethers. In that case the reaction temperatures are higher and the yields lower.

4. Conversion of the allyl alcohols of the formula III into 1-alkoxy-2,6-dimethyl-2,6-octadienyl halides, followed by an acetoacetic acid ester synthesis.

atmospheric pressure or the slightly superatmospheric pressure under which the phosgene is introduced.

Examples of N,N-dialkyl-substituted low molecular weight fatty acid amides are N,N-dimethylformamide, N,N-diethylformamide, N,N-dimethylacetamide and N,N-dibutylpropionamide, whilst N-methylpyrrolidone and N-ethylcaprolactam may be mentioned as examples of N-alkylated lactams. To carry out the process, e.g., a mixture of compound III and the carboxylic acid amide is introduced into a suitable solvent. The phosgene is then introduced at room temperature, or the thionyl chloride is added slowly. However, it is also possible to take a mixture of the carboxylic acid amide with the chlorinating agent and to add compound III.

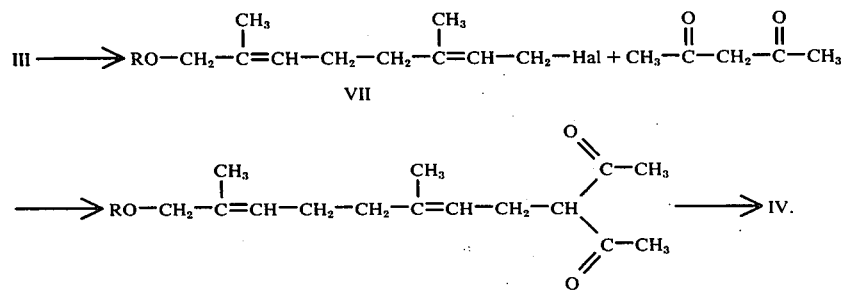

The conversion of the allyl alcohols III to the said halides may be carried out, e.g., in accordance with the processes described in Chem. Reviews 56 (1956), 801 to 818, which lead to a primary halide. Such is generally the case if the reaction mixture is acid. Examples of suitable halogenating agents are HBr (aqueous or gaseous), $PBr_3$, $PBr_5$, $SOBr_2$, HCl (aqueous or gaseous), $PCl_3$, $PCl_5$, $SOCl_2$, $COCl_2$ and HI. In the case of some halogenating agents, 1-alkoxy-2-methyl-but-3-ene-2-halides are formed at low temperatures and/or in the presence of basic compounds. These halides can be rearranged to the halides VII by treatment with an acid catalyst at from −50° to +200° C.

Examples of acid catalysts are proton acids having a $pK_A$ less than about 6, e.g. aliphatic or aromatic carboxylic acids, such as acetic acid, chloroacetic acid, trichloroacetic acid, trifluoroacetic acid and benzoic acid, aliphatic or aromatic sulfonic acids, e.g. methanesulfonic acid or p-toluene-sulfonic acid, inorganic acids, such as hydrogen halide acids (HCl and HBr), sulfuric acid, phosphoric acid, polyphosphoric acid, perchloric acid, acid ion exchangers, zeolites or bleaching earths, and also Lewis acids, such as $BF_3$, $AlCl_3$, $ZnCl_2$ and the like.

The acid is in general used in amounts of from 0.001 to 0.5 mole per mole of III, either undiluted or in aqueous solution. The reaction temperature can be from −50° to +200° C and the reaction time may vary from 0.1 to 20 hours. Both parameters depend very greatly on the strength ($pK_A$ value) and amount of the acid used as the catalyst.

As an example of a conversion of allyl alcohols III to the halides VII, the conversion of III analogously to the process for the manufacture of allyl chlorides in German Patent 1,162,354 will be discussed in more detail. According to this process, a compound III is converted in the presence of N,N-dialkyl-substituted amides of low molecular weight fatty acids or N-alkyl-substituted lactams, if appropriate in an inert solvent.

The reaction is in general carried out at from about −50° to +50° C, preferably from −20° to +20° C, and at The reaction mixture is worked up, e.g., by adding water, separating off the organic phase, evaporating the solvent and fractionating the residue, if the latter is distillable. Solvents which can be used are aliphatic or aromatic hydrocarbons as well as chlorinated hydrocarbons and ethers. The amount of solvent can be varied within wide limits. When using liquid allyl alcohols the process can also be carried out without solvents. The chlorinating agent is advantageously employed in slight excess over the allyl alcohol. The N-substituted carboxylic acid amides of N-alkylated lactams are added in amounts of, e.g., from 0.01 to 1 mole per mole of chlorinating agent, but even larger amounts can be used, in which case the acid amide acts as the solvent.

The alkoxyketones IV are obtained by reacting the halides, obtained above, with alkali metal compounds of acetoacetic acid esters and subsequently splitting off the —COOR' group from the substituted acetoacetic acid esters by alkaline thermal scission.

The alkali metal compounds of an acetoacetic acid ester are advantageously the alkali metal derivatives of acetoacetic acid esters of lower alcohols, ie. the esters of alcohols of 1 to 4 carbon atoms, especially of 1 or 2 carbon atoms. The use of higher esters is possible but produces no significant advantages.

The alkali metal compounds of the acetoacetic acid ester are manufactured by conventional methods, e.g. by reacting the acetoacetic acid ester with an alkali metal hydroxide or alkali metal alcoholate at from 0° to 50° C.

Preferred alkali metal compounds of an acetoacetic acid ester are the sodium compound and the potassium compound of methyl acetoacetate and of ethyl acetoacetate.

The reaction of the halides VII with the alkali metal compound of an acetoacetic acid ester can be carried out in various ways.

In general, from about 0.9 to 1.2 moles of the halide of the formula VII, per mole of ester, are added to the solution or suspension of the alkali metal acetoacetic acid ester at from 0° to 100° C, preferably from 10° to 60° C. The reaction requires a reaction time of from 0.5 to 15 hours. It may be carried out batchwise or continuously. Examples of suitable solvents or suspending agents are alcohols, e.g. methanol, ethanol, propanol, butanol, isobutanol and glycol, or hydrocarbons, e.g. benzene, cyclohexane, hexane and decalin. However, ethers, e.g. diethyl ether and tetrahydrofuran, can also be used as solvents. Alcohols, especially methanol or ethanol, are however particularly advantageous solvents.

It is also possible slowly to introduce the alkali metal compound of an acetoacetic acid ester, in the form of a powder, into the halide of the formula VII, with thorough mixing. A time of from 0.5 to 5 hours is required to introduce the alkali metal compound. The total reaction time is from 0.5 to 15 hours.

The intermediate products obtained from the reaction of the alkali metal compound of an acetoacetic acid ester with the halide VII do not have to be isolated before being processed further.

To split off the alkoxycarbonyl group, it is advantageous to add an aqueous alkali metal hydroxide solution to the reaction mixture obtained from the reaction described above and to heat the mixture at from 20° to 100° C, preferably from 30° to 80° C. In general, from 1 to 4 moles, preferably from 1 to 2 moles, of alkali metal hydroxide in the form of a solution of from 5 to 20 per cent strength, preferably of about 10 per cent strength, are used per mole of ester. The reaction time required to split off the —COOR$^3$ group is from 0.5 to 10 hours.

If an alcohol has not been employed as the solvent in the course of the manufacture of the substituted acetoacetic acid esters, it is advantageous to employ a lower alcohol, e.g. methanol, as a solubilizing agent in the reaction in which the alkoxycarbonyl is split off. The amount required corresponds approximately to the amount by weight of water present in the reaction mixture. It was surprising that the COOR$^3$ group could be split off merely by alkaline treatment, since such reactions usually require an additional treatment with acids.

C. The vinylation or ethynylation and subsequent partial hydrogenation of the alkoxyketones of the formula IV to give the allyl alcohols of the formula V may be carried out in the manner described under A).

D. The elimination of water from the resulting allyl alcohols of the formula V may be effected, e.g., by dropwise addition of the alcohols V to a suspension or solution of acids or Lewis acids such as KHSO$_4$, CuSO$_4$, adipic acid, p-toluenesulfonic acid and the like, in an inert solvent, e.g. paraffin oil, at from 150° to 200° C, and distillation of the water formed and of the reaction product under reduced pressure.

The elimination of water can furthermore be effected by boiling with acids, e.g. H$_2$SO$_4$, or with dehydrating agents, e.g. P$_2$O$_5$ or acetic anhydride.

It is also possible to carry out the reaction with said chlorides, e.g. POCl$_3$ or SOCl$_2$, in the presence of amines, e.g. pyridine or quinoline.

The reaction in which water is eliminated in general gives a mixture of isomers, in which the ratio of I$a$ to I$b$ is about 2:1. Furthermore, cis-trans isomers are present.

The new 12-alkoxy-3,7,11-trimethyldodecatetraenes can furthermore be manufactured from the 7-alkoxy-6-methyl-hept-5-en-2-ones of the formula II by reacting them, in a Wittig reaction, with a triarylphosphonium halide of the general formula VIII

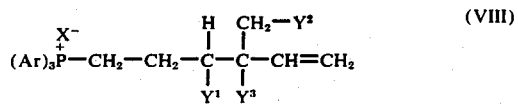

where Ar is phenyl or toluyl, X is Cl, Br or I and Y$^1$ and Y$^2$ are different and each is hydrogen or together with Y$^3$, is an additional bond between the carbon atoms carrying Y$^1$ and Y$^3$, or Y$^2$ and Y$^3$, respectively.

The phosphonium salts of the formula VIII may be manufactured in various ways. For example, they are obtained by Grignard vinylation of 1-halo-pentan-4-one, subsequent elimination of water from the alcohol obtained and reaction of the resulting halogen compound with triphenylphosphine in an inert solvent, e.g., benzene, toluene, xylene or gasoline, at from 40° to 200° C. This gives the triphenylphosphonium salt in the form of 2-double bond isomers, and as a result the reaction with the 7-alkoxy-6-methyl-hept-5-en-2-ones of the formula II leads to the formation of a mixture of the isomeric compounds of the formulae I$a$ and I$b$.

Isomers of the formula I$a$ are obtained exclusively when the 7-alkoxy-6-methyl-hept-5-en-2-ones of the formula II are reacted with a triphenylphosphonium salt which is obtained, by conventional methods, by heating equimolar amounts of triphenylphosphine and 1-bromo-4-methyl-3,5-hexadiene in an inert solvent, e.g. tetrahydrofuran, toluene or petroleum ether, for from 1 to 5 days, and filtering off the salt which precipitates.

The required 1-bromo-4-methyl-3,5-hexadiene can be manufactured by reacting methylcyclopropyl-vinylcarbinol with HBr at 0° C or even lower temperatures.

To carry out the Wittig reaction of the invention, the phosphonium salts are first dissolved or suspended in an inert organic solvent and approximately an equimolar amount of a strong base is then added to this solution or suspension at from −50° to +100° C, preferably from −20° to +30° C. A deep red color of the reaction mixture indicates the formation of the corresponding triphenylphosphinylenes.

Suitable inert solvents are hydrocarbons, e.g. benzene and toluene, ethers, e.g. diethyl ether, ethylene glycol dimethyl ether and tetrahydrofuran, and strongly polar solvents such as dimethylformamide, N-methylpyrrolidone and alcohols, e.g. methanol and ethanol.

Examples of strong bases which can be used are butyl lithium, methyl-magnesium chloride, sodium alcoholates and potassium alcoholates, sodium hydride, sodium amide, sodium hydroxide and potassium hydroxide.

The triphenylphosphinylenes obtained do not have to be isolated before being reacted further.

The ketones of the formula II are then added to the resulting solution of the ylenes at from −20° to 100° C, preferably from 10° to 70° C. The reaction of the ylenes and the ketones as a rule takes place instantly. Towards the end of the reaction, the reaction mixture has a yellow color.

To achieve maximum possible conversion, the ylenes are employed in a slight stoichiometric excess (from about 5 to 10%).

The reaction mixture is worked up in the usual manner. For example, water is added to the reaction mixture obtained, the batch is extracted with petroleum ether, the sparingly soluble triphenylphosphine oxide is filtered off, and the products are isolated by distillation.

The 12-alkoxy-3,7,11-trimethyldodecatetraenes according to the invention, of the formula I, are valuable perfume and flavoring compounds with an orangey-fruity, green, piney note, and may be used as additives for improving scents and flavors.

EXAMPLE 1

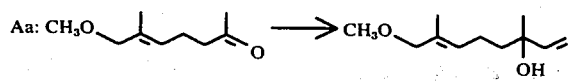

141 g (0.9 mole) of 7-methoxy-6-methyl-oct-5-en-2-one are added to 1 mole of a 1.5 normal solution of vinyl-magnesium chloride in tetrahydrofuran, at below 20° C, in the course of one hour. After a further 2 hours' reaction, hydrolysis is carried out with 100 ml of water, whilst cooling with ice. After a homogeneous salt suspension has formed, the salt and the tetrahydrofuran solution are separated by filtering or centrifuging. The tetrahydrofuran is distilled off under reduced pressure and the reaction product which remains is purified by fractional distillation. 164 g of 8-methoxy-3,7-dimethyl-octa-1,6-dien-3-ol (yield 85%) are obtained. Boiling point 73°–75° C/0.01 bar; $n_D^{25}$ = 1.4676.

Odor: fresh-floral, slightly fruity, mildly linalool-like.
Bl:

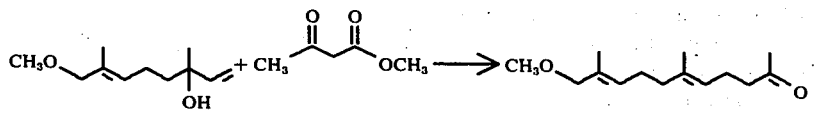

116 g (1 mole) of methyl acetoacetate are added to 92 g (0.5 mole) of 8-methoxy-3,7-dimethyl-octa-1,6-dien-3-ol and the mixture is heated from 160° C to 190° C in the course of about 2.5 hours, whilst stirring. The methanol liberated is distilled through a 10 cm column and the $CO_2$ is measured by means of a gas flowmeter. After the reaction has ended, the reaction mixture is purified by fractional distillation, giving 74 g of 11-methoxy-6,10-dimethyldeca-5,9-dien-2-one (yield 66%).

Boiling point 93° C/0.01 bar, $n_d^{25}$ = 1.4699.
Odor: juniper berries, suggestive of gin.
Ca:

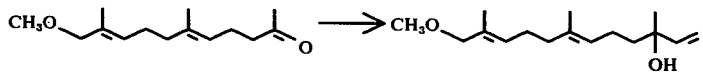

67 g (0.3 mole) of 11-methoxy-6,10-dimethylundeca-5,9-dien-2-one are reacted with 0.4 mole of vinyl-magnesium chloride as described in Aa, and the mixture is worked up accordingly. 69 g of 12-methoxy-3,7,11-trimethyl-dodeca-1,6,10-trien-3-ol are obtained (yield 92%).

Boiling point 120°–122° C/0.01 bar, $n_D^{25}$ = 1.4791
Odor: fruity-sweet, slightly earthy, herbaceous.
D: Mixture of

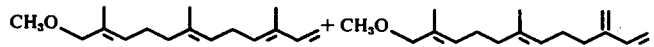

5 g of copper sulfate pentahydrate are suspended in 20 g of paraffin oil, with vigorous stirring, and the suspension is heated at 180° C under 20 mm Hg. The water of crystallization which is eliminated is removed through a descending condenser. After the reaction has ended, 25 g (0.1 mole) of 12-methoxy-3,7,11-trimethyl-dodeca-1,6,10-trien-3-ol are added dropwise to the suspension and water and reaction product are distilled off simultaneously (reaction time about 30 minutes). After completion, the distillate is taken up in 100 ml of ether, the ether solution is washed with sodium carbonate solution, then washed neutral with water and dried over sodium sulfate, and the drying agent is then filtered off. After distilling off the ether, the product which remains is fractionated, giving 11 g of a 2:1 mixture of 12-methoxy-3,7,11-trimethyl-dodeca-1,3,6,10-tetraene and 12-methoxy-3-methylene-7,11-dimethyl-dodeca-1,6,10--triene (yield 47%).

Boiling point 92°–96° C/0.15 bar, $n_D^{25}$ = 1.5095.
The isomer content is determined by nuclear resonance spectroscopy.
Odor: orangey-fruity, green, piney.

EXAMPLE 2

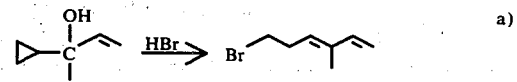

140 g of cyclopropyl-vinyl-methyl-carbinol are slowly added dropwise, at −10° C, to 550 ml of a 48 per cent strength aqueous solution of HBr. The reaction mixture is then stirred for a further hour at this temperature and covered with 200 ml of petroleum ether, the organic phase is separated off and the aqueous phase is extracted twice more with 200 ml of petroleum ether at a time. The combined organic phases are washed with water, dried over sodium sulfate and concentrated. Distillation gives 188 g (86%) of 1-bromo-4-methyl-hexa-3,5-diene of boiling point 72° C/13 mm Hg, in which product the isomer ratio is 85% trans and 15% cis (according to the nuclear resonance spectra).

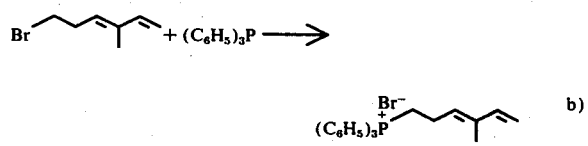

56.5 g of 1-bromo-4-methyl-hexa-3,5-diene and 88 g of triphenylphosphine in 200 ml of tetrahydrofuran are boiled under reflux for 4 days. Diethyl ether is added and the salt which has precipitated is filtered off and dried in a desiccator.

95 g (67%) of melting point 167°–170° C are obtained.

The salt must be stored in a dark bottle, as it otherwise decomposes slowly.

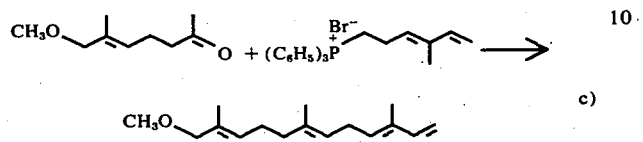

c)

50 g of the salt obtained are suspended in 300 ml of tetrahydrofuran. 80 ml of 1.5 normal n-butyl-lithium solution in hexane are added dropwise under a nitrogen atmosphere, whilst cooling with ice. The salt dissolves, giving a deep red color. After stirring for a further hour at room temperature, 18 g of 7-methoxy-6-methyl-hept-5-en-2-one are added dropwise and the reaction mixture is boiled under reflux for 3 hours, until the red color has almost disappeared. The tetrahydrofuran is distilled off under reduced pressure and the residue is extracted with 3 100 ml portions of petroleum ether. The petroleum ether solution is washed with water, dried over sodium sulfate and concentrated. The product is purified by distillation. 14 g (51%) of 12-methoxy-3,7,11-trimethyl-dodeca-1,3,6,10-tetraene, boiling at 104°–110° C/0.3 mm Hg, are obtained. The proportion of cis 2-double bonds is 15%, and the ratio of the cis-trans isomers at the 6-double bond is about 50:50.

What we claim is:

1. A compound of the general formula I

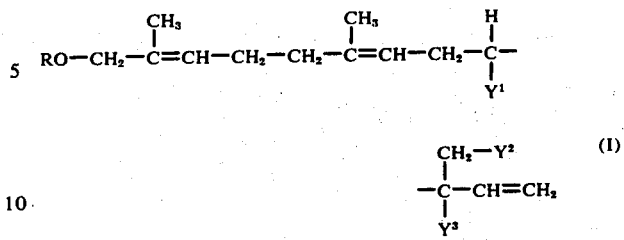

where R is $CH_3$, $C_2H_5$, n-$C_3H_7$ or iso-$C_3H_7$ and $Y^1$ and $Y^2$ are different and each is hydrogen or, together with $Y^3$, is an additional bond between the carbon atoms carrying $Y^1$ and $Y^3$, or $Y^2$ and $Y^3$, respectively.

2. A mixture of the isomeric compounds of the general formula Ia and Ib

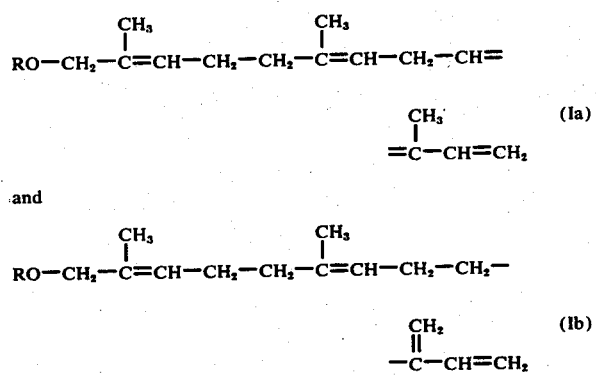

where R is $CH_3$, $C_2H_5$, n-$C_3H_7$ or iso-$C_3H_7$.

* * * * *